(12) United States Patent
Turner et al.

(10) Patent No.: US 8,423,152 B2
(45) Date of Patent: Apr. 16, 2013

(54) APPARATUS AND METHOD FOR SELECTIVELY HEATING A DEPOSIT IN FATTY TISSUE IN A BODY

(75) Inventors: Paul F. Turner, Bountiful, UT (US); Mark Hagmann, Salt Lake City, UT (US)

(73) Assignee: BSD Medical Corporation, Salt Lake City, UT (US)

( * ) Notice: Subject to any disclaimer, the term of this patent is extended or adjusted under 35 U.S.C. 154(b) by 1274 days.

(21) Appl. No.: 12/152,513

(22) Filed: May 14, 2008

(65) Prior Publication Data

US 2008/0319437 A1 Dec. 25, 2008

Related U.S. Application Data

(60) Provisional application No. 60/930,329, filed on May 14, 2007.

(51) Int. Cl.
*A61N 5/00* (2006.01)
(52) U.S. Cl.
USPC .......................................................... 607/101
(58) Field of Classification Search .......... 607/100–101, 607/154, 156
See application file for complete search history.

(56) References Cited

U.S. PATENT DOCUMENTS

| | | | |
|---|---|---|---|
| 5,097,844 A | 3/1992 | Turner | |
| 5,231,997 A | 8/1993 | Kikuchi et al. | |
| 5,540,737 A * | 7/1996 | Fenn | 607/101 |
| 5,928,159 A | 7/1999 | Eggers et al. | |
| 6,131,577 A | 10/2000 | Nicholson | |
| 6,163,726 A | 12/2000 | Wolf | |
| 6,275,738 B1 | 8/2001 | Kasevich et al. | |
| 6,347,251 B1 | 2/2002 | Deng | |
| 6,358,246 B1 | 3/2002 | Behl et al. | |
| 6,391,026 B1 | 5/2002 | Hung et al. | |
| 6,413,204 B1 | 7/2002 | Winkler et al. | |
| 6,425,912 B1 | 7/2002 | Knowlton | |
| 6,468,273 B1 | 10/2002 | Leveen et al. | |
| 6,470,217 B1 | 10/2002 | Fenn et al. | |
| 6,494,844 B1 | 12/2002 | VanBladel et al. | |
| 6,690,976 B2 | 2/2004 | Fenn et al. | |

(Continued)

OTHER PUBLICATIONS

Barry et al.; Challenges in the Development of Magnetic Particles for Therapeutic Applications; Int J. Hyperthermia; Sep. 2008; vol. 24, No. 6; pp. 451-466.

(Continued)

*Primary Examiner* — Laura A Bouchelle
*Assistant Examiner* — Melissa A Snyder
(74) *Attorney, Agent, or Firm* — Thorpe North & Western LLP

(57) ABSTRACT

An apparatus and method for providing hyperthermia treatments to a protruding body portion having fatty tissue surrounding a deposit in the protruding body portion is disclosed. The apparatus includes a cavity for receiving the protruding body portion. A radio frequency antenna array is used to direct a radio frequency signal at a selected frequency into the protruding body portion such as a breast so that the radio frequency signal will have a selected wavelength in the breast to create a circularly polarized radio frequency electromagnetic field to selectively heat the deposit to a temperature greater than the surrounding fatty tissue through resonant heating within the deposit when a diameter of the deposit is within a range of about 0.5 times to 0.16 times the wavelength of the radio frequency signal within the fatty mammary tissue.

21 Claims, 5 Drawing Sheets

U.S. PATENT DOCUMENTS

| | | | |
|---|---|---|---|
| 6,712,816 | B2 | 3/2004 | Hung et al. |
| 6,725,095 | B2 | 4/2004 | Fenn et al. |
| 6,768,925 | B2 | 7/2004 | Fenn et al. |
| 6,904,323 | B2 | 6/2005 | Samulski |
| 6,923,754 | B2 | 8/2005 | Lubock |
| 6,945,942 | B2 | 9/2005 | Van Bladel et al. |
| 7,354,391 | B2 | 4/2008 | Stubbs |
| 7,510,555 | B2 | 3/2009 | Kanzius |
| 2006/0269612 | A1 | 11/2006 | Xiang et al. |
| 2007/0168001 | A1 | 7/2007 | Xiang et al. |
| 2008/0045865 | A1 | 2/2008 | Kislev |
| 2008/0319437 | A1 | 12/2008 | Turner et al. |
| 2009/0306646 | A1 | 12/2009 | Turner |
| 2010/0100092 | A1 | 4/2010 | Turner |

OTHER PUBLICATIONS

Denardo et al., "Thermal dosimetry predictive of efficacy of 111In-ChL6 nanoparticel AMF-induced thermoablative therapy for human breast cancer in mice" Journal of Nuclear Medicine, Mar. 2007, vol. 48, No. 3, pp. 437-444.

Dewhirst, "Hyperthermia and nanotechnology—a note from the editor-in-chief" Int. J. Hyperthermia, Sep. 2008, vol. 24 No. 6, pp. 449-450.

Gannon et al.; Carbon Nanotube-enhanced Thermal Destruction of Cancer Cells in a Noninvasive Radiofrequency field; Wiley InterScience (www.interscience.wiley.com) Oct. 24, 2007; pp. 2654-2665.

Gannon et al.; Intracellular Gold Nanoparticles Enhance Non-Invasive Radiofrequency Thermal Destruction of Human Gastrointestinal Cancer Cells; Journal of Nanobiotechnology 2008; 6:2; 9 pages.

Huang et al., "The influence of single-walled carbon nanotube structure on the electromagnetic interference shielding efficiency of its epoxy composites" 2007, 7 pages.

Ivkov et al., "Application of high amplitude alternating magnetic fields for heat induction of nanoparticles localized in cancer" Clin Cancer Res, 2005, pp. 7093-7103, vol. 11.

Klingeler et al., "Carbon nanotube based biomedical agents for heating, temperature sensing and drug delivery" Int. J. Hyperthermia, Sep. 2008, pp. 496-505, vol. 24, No. 6.

Laloup; http://www.wired .com/medtech/health/news/2008/04/kanzius_therapy; Apr. 13, 2008; 2 pages.

McLachlan et al., "The AC and DC conductivity of nanocomposites" Journal of Nanomaterials, 2007, vol. 2007, 9 pages.

Mdarhri et al., "Microwave properties of multiwall carbon nanotubes filled polymers" Journal of microwaves and optoelectronics, Jun. 2007, pp. 38-43, vol. 6, No. 1.

Moran et al.; Size Dependent Joule Heating of Gold Nanoparticles Using Capacitively Coupled Radiofrequency Fields; Nano Res; 2009; vol. 2 pp. 400-405.

Ott et al., "Radiochemotherapy for bladder cancer" Clinical Oncology, 2009, pp. 557-565, vol. 21.

Sandler et al.; Ultra-Low Electrical Percolation Threshold in Carbon-Nanotube-Epoxy Composites; Polymer; 2003; vol. 44; pp. 5893-5899.

Sundararman et al; The Modification of Specific Absorption Rates in Interstitial Microwave Hyperthermia via Tissue-Equivalent Material; Int J Radiat Oncol Biol Phys; Sep. 1990; vol. 3; pp. 677-685.

Thiesen et al., "Clinical applications of magnetic nanoparticles for hyperthermia" Int. J. Hyperthermia, Sep. 2008, vol. 24 No. 6 pp. 467-474.

USAF School of Aerospace Medicine; Radiofrequency Radiation Dosimetry Handbook; Report SAM-TR-76-35; Sep. 1976; 10 pages.

USAF School of Aerospace Medicine; Radiofrequency Radiation Dosimetry Handbook; Second Edition Report SAM-TR-78-22; May 1978; 9 pages.

Von Maltzahn et al.; Computationally Guided Photothermal Tumor Therapy Using Long-Circulating Gold Nanorod Antennas; Cancer Res; May 1, 2009; vol. 69, No. 9; 9 pages.

U.S. Appl. No. 12/479,670, filed Jun. 5, 2009; Paul F. Turner; office action issued Mar. 29, 2012.

U.S. Appl. No. 12/646,729, filed Dec. 23, 2009; Paul F. Turner; office action issued May 21, 2012.

U.S. Appl. No. 12/479,670, filed Jun. 5, 2009; Paul F. Turner; office action issued Oct. 17, 2011.

* cited by examiner

APPARATUS AND METHOD FOR SELECTIVELY HEATING A DEPOSIT IN FATTY TISSUE IN A BODY

CROSS-REFERENCE TO RELATED APPLICATIONS AND CLAIM OF PRIORITY

Priority of U.S. Provisional patent application Ser. No. 60/930,329 filed on May 14, 2007 is claimed, which is herein incorporated by reference in its entirety.

TECHNICAL FIELD

The present invention generally relates to inducing hyperthermia in a desired target such as cancerous tumor tissue. More particularly, the present invention relates to non-invasively causing localized hyperthermia in a tumor-containing tissue using an array of antenna structures positioned outside the tumor-containing tissue.

BACKGROUND

Certain types of cancerous tumors, such as breast cancer tumors, particularly inflammatory and locally advanced tumors, often resist traditional treatments. It has been statistically shown that sixty to seventy percent of victims of such breast tumors do not survive past five years. The efficacy of conventional methods of treating cancer, such as radiotherapy and chemotherapy, is limited due to necessary constraints on dosage amounts for safety.

For example, it is known that chemotherapy can be applied in sufficient amounts to kill virtually all cancer cells of a tumor. However, the amounts of chemotherapy needed to achieve this can be high enough to cause poisoning of the patient and/or undue side effects. As another example, the intensity of an x-ray beam applied in accordance with radiotherapy cannot be set at an intensity that will damage nearby critical organs and surrounding healthy tissues. Accordingly, there is an ongoing need to develop techniques that enhance existing cancer-related therapeutic procedures so as to increase their effectiveness without increasing the risk of damage to healthy tissue and causing additional discomfort for cancer patients. Breast tumors that have grown to a size of about 3 cm to about 5 cm are particularly hard to treat and are hard to remove surgically, generally requiring removal of the breast to remove the tumor. Alternative treatments for such tumors are needed.

One recent approach toward improving cancer therapy is to subject a tumor to a hyperthermia treatment, i.e., heating of the tumor. The application of heat to cancer cells has been found to increase the efficacy of certain types of therapies for various proposed reasons. Microwave and radio frequency (RF) energy sources have been employed to conduct hyperthermia treatment. Microwave energy has been applied to tumors using waveguides. However, the relatively high frequencies at which microwaves propagate are generally not suitable for deep penetration into tissue. RF energy at a lower frequency has also been utilized in some instances, and has the potential to achieve greater penetration due to its relatively lower frequencies. However, both microwave and RF techniques have typically used invasive elements, such as wires, catheters, lumens, probes, receivers, and the like. These invasive elements are usually inserted or embedded in the tumor to be treated to ensure proper coupling and focusing of the electromagnetic energy at the tumor site. The use of invasive elements adds complexity to the procedure and is a source of discomfort for patients. Examples of invasive heating techniques using microwave and RF energy are disclosed in U.S. Pat. Nos. 5,928,159; 6,275,738; 6,358,246; 6,391,026; 5,540,737, and 6,468,273.

One prior method for hyperthermia treatment involves the use of phased arrays of dipoles surrounding portions of a body in which a selected portion, such as a tumor, is desired to be heated. The dipoles are operated in a coherent phase or at least a synchronous phase relationship to enable selective targeting of deep tissue tumor masses by controlling the power and relative phase applied to the array of dipoles. These dipoles couple their RF or microwave energy to the body through typically deionized water media as it is high in dielectric constant similar to most of the body tissues but is lower in electrical conductivity so it provides small wavelengths but low power absorption. The antenna arrays surrounding such tissue structures have generally been in concentric arrays using lower frequencies with long wavelengths or have been at high frequencies, at or near microwave frequencies including breast compression, but not in arrangements that would produce selective resonant behavior in tumors of the breast nor create circular polarization that would improve uniformity of such tissue target heating.

Samulski, in U.S. Pat. No. 6,904,323, described the use of phased array dipoles that are place around a cavity containing fluid such as water and where a human breast containing a cancerous tumor can be submerged and heated by the surrounding dipoles antennas. This method uses rather low frequencies that produce a very large wavelength in both high water tissues of the body and in low water content tissues such as mammary fat. The operation, typically at a frequency of about 140 MHz results in a wavelength in fatty tissue of about 86 cm and in muscle tissues is 22.9 cm.

It is desirable to provide a method and apparatus for non-invasively inducing hyperthermia in tumors and malignant tissues that reside within a breast or other protruding portion of a body while avoiding or at least decreasing the potential of excessively heating the surrounding fatty mammary tissue.

SUMMARY

An apparatus and method for providing hyperthermia treatments to a protruding body portion having fatty tissue surrounding a deposit such as a tumor, cyst, or high conductivity implant in the protruding body portion is disclosed. The apparatus includes a cavity for receiving the protruding body portion. A radio frequency signal generator operable to generate a radio frequency signal is used. The signal generator can output a radio frequency signal that will have a selected wavelength within the fatty tissue. The wavelength is in a range of about 3.75 to 2.25 times a diameter of the deposit. A radio frequency antenna array is used to direct the radio frequency signal into the breast to create a circularly polarized radio frequency electromagnetic field to selectively heat the deposit to a temperature greater than the surrounding fatty tissue through resonant heating within the deposit from the radio frequency signal having the selected wavelength.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
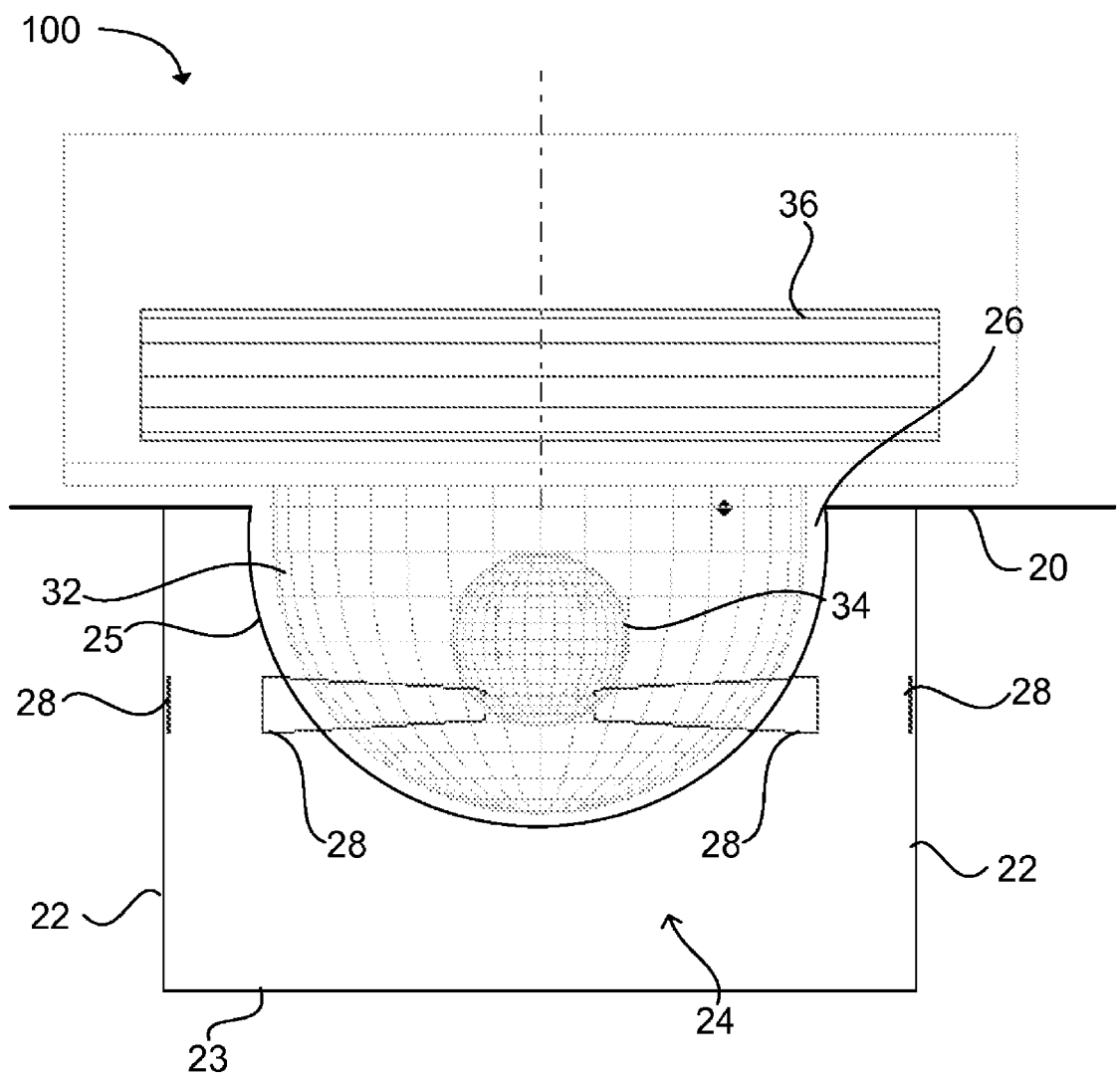
FIG. 1 is a front schematic illustration of an apparatus in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Tumors in the breast or other protruding body parts can be selectively heated by directing RF or microwave energy to the body part with a frequency high enough to promote resonant energy absorption in the tumor tissue as compared to the surrounding tissue. Selective heating is particularly successful where the tumor tissue to be heated has relatively high water content compared to the surrounding non-tumor tissue. This enhanced energy absorption relates to a sub-resonant condition behavior of the relatively high water content tissue due to the fact that low water content tissues of the body has rather low electrical conductivity, dielectric constant, and energy absorption with depth as compared to higher water content tissue such as muscle and tumor tissues. The lower dielectric constant results in a longer wavelength in such tissues for all frequencies in the RF and microwave frequency range, with a shorter wavelength in the higher dielectric constant tumor tissue. The higher conductivity tissue can resonate in a relatively small cavity, such as a tumor.

Resonance is a well understood phenomenon that is used to receive and amplify electromagnetic field waves in standard RF and microwave antennas. The antennas are electrical conductors used to enhance electrical currents induced when exposed to electromagnetic fields that have a wavelength that is n times a 1/n ratio of the size of the antenna, where n is a positive integer. The strongest whole object resonance can occur when the wavelength is two times the antenna length for a wire antenna. The use of resonance to amplify an electromagnetic field has not been reported or studied for tissue structures submerged in the human body. The inventors have discovered that such relationships do occur and can be utilized to provide enhanced and even selective heating of more conductive and higher dielectric constant tissue masses that are surrounded by less electrically conductive and lower dielectric constant tissues.

One aspect of the present invention is the use of this special phenomena that provides selective heating of a relatively small high water content tumor mass that is surrounded by larger, drier tissues such as mammary tissue or fat. An advantageous application of the present invention is the enhanced level of RF or microwave energy absorption within a tumor of high water content as compared to the surrounding tissues, such as exists in a female breast.

The term radio frequency (RF) generically means electromagnetic radiation with an alternating electric current. It has been common in recent years to define RF extending from frequencies as low as 3 Hz to 300 GHz. The microwave frequency range has been defined to start at various lower frequencies from as low as 300 MHz for some sources and starting at 1000 MHz for others. Therefore, the terms are not very specific to use and use of a specific frequency range becomes important when referring to a resonant type of phenomena that leads to selective energy absorption. The term radio frequency or RF will generally be used in this specification, with specific frequencies or frequency ranges of the alternating electric current in the electromagnetic energy disclosed.

One embodiment of an apparatus 100 for providing hyperthermia treatment for selectively heating tumors located in a protruding portion of a human body is illustrated in FIG. 1. The apparatus comprises an applicator body 25 and a plurality of antennas 28. The applicator body has a concave profile extending from an aperture 26, and defines an open cavity 24 for receiving RF or microwave circularly or elliptically polarized waves. The antennas are operatively associated with the applicator body and are arrayed for transmitting RF or microwave waves at respective selected amplitudes and relative phases into the cavity. The cavity is typically a fluid filled cavity. The electromagnetic energy from the arrayed antennas is generally directed toward a tumor-containing tissue to produce a circularly or elliptically polarized field that will be selectively absorbed by the high water content tissues of a tumor of a size that is partially resonant with the applied fields and their wavelength of the surrounding low water content media.

In order to optimize the amount of resonant energy that is absorbed in a cancerous mass, a specific wavelength of electromagnetic radiation can be selected that is approximately 3 times greater than a diameter of the mass. However, in most countries, the use of the electromagnetic spectrum is heavily regulated. The radio frequency spectrum has been divided into bands, with each band or frequency typically allowed to be used only for a specific application. The frequency of 915 MHz is an approved frequency for use in hyperthermia treatments in the United States and many other countries.

The wavelength of RF radiation at a frequency of 915 MHz is approximately 14 cm in the fatty tissues of the female breast. This mammary fatty tissue is the dominant tissue of the breast. The wavelength of high water tissues such as muscle material at 915 MHz is approximately 4.36 cm. The table below shows typical values for the RF frequency of 915 MHz for wavelength, penetration, and conductivity in different types of tissue, as published by various sources.

| Source | Tissue | Freq (MHz) | Diel. | Cond. S/m | Wave length (cm) | Penetration (cm) |
|---|---|---|---|---|---|---|
| Guy | Breast/Fat | 915 | 5.6 | .056-.15 | 13.7 | 17.7 |
| Guy | Muscle | 915 | 51 | 1.60 | 4.46 | 3.04 |
| IFAC | Breast/Fat | 915 | 5.42 | 0.050 | 14 | 25 |
| IFAC | Muscle | 915 | 55 | .948 | 4.35 | 4.2 |
| Gabriel | Breast/Fat | 915 | 5.42 | .050 | 14 | 25 |
| Gabriel | Muscle | 915 | 55 | .948 | 4.35 | 4.2 |

| Tissue Value Comparisons of Dielectric Constant | | | | | | |
|---|---|---|---|---|---|---|
| Tissue | Freq (MHz) | Guy | IFAC | Gabriel | Joines | Pethig |
| Breast/Fat | 915 | 5.6 | 5.42 | 5.42 | 15 | 5.6 |
| Muscle | 915 | 51 | 55 | 55 | 57.1 | 46 |

| Tissue Value Comparisons of Conductivity (S/m) | | | | | | |
|---|---|---|---|---|---|---|
| Tissue | Freq (MHz) | Guy | IFAC | Gabriel | Joines | Pethig |
| Breast/Fat | 915 | .056-.15 | .050 | .050 | .18 | .083 |
| Muscle | 915 | 1.60 | .948 | .948 | 1.16 | 1.28 |

As previously discussed, electromagnetic frequencies having a selected wavelength can resonate within an object of a selected size. When the object is an inner object having a higher conductivity and a higher relative dielectric constant that is contained within a larger object having a lower relative conductivity and a lower relative dielectric constant, the smaller inner object may receive substantially more power from an electromagnetic field due to its size and conductivity.

For example, in a tumor contained within a female breast, the tumor diameter can have a diameter approaching 4.5 cm. This tumor, which has a higher water content than the surrounding fatty breast tissue, may therefore experience a self resonant condition leading to increased tumor heating relative to the fatty breast tissue due to the increased resonant currents at a frequency of 915 MHz. This resonant behavior may also be expected to occur at diameters larger than this but with less intensity. So it is reasonable to consider that tumors near this resonant size condition of approximately between 3 to 6 cm in diameter may experience some selective heating due to the resonance of the tumor mass that is surrounded by fatty mammary tissue.

This behavior is similar to a resonant antenna in free space. The phenomena of body resonance for a human body was observed and reported in a U.S. Air Force commissioned study at the University of Utah in 1976, as reported in SAM-TR-76-35 and SAM-TR-78-22 (1978) page 101, which is herein incorporated by reference. In this report, it is shown that a prolate spheroidal model of a chicken egg would be of major axis size 5.8 cm and minor size diameter of 4.4 cm. When the chicken egg is located in an air medium and exposed to a 2 GHz field it becomes resonant with the field. On resonance in an electromagnetic field having an intensity of 1 milliwatt per centimeter squared (mW/cm$^2$), the specific absorption rate (SAR) of the egg is between 0.35 to 0.46 Watts/kg. At higher frequencies, where the egg diameter is no longer resonant due to the shorter wavelength of the RF signal, the absorption drops to about 0.11 W/kg.

The free space wavelength of an RF signal at a frequency of 2 GHz is 15 cm. So the resonant diameter size of the spheroid object is between 0.293 to 0.386 times the wavelength, or in other words approximately one fourth to one third of the wavelength. The free space wavelength of an RF signal at a frequency of 915 MHz is approximately 32.8 cm. The spherical resonance size for 915 MHz when surrounded by free space would be expected to be between 9.6 to 13.0 cm. This is calculated based on simple frequency scaling.

For the condition that a spheroid, such as a cancerous tumor having a higher conductivity and dielectric, is contained within a uniform media such as fatty breast tissue that has a dielectric constant greater than free space, the resonant conditions can occur for a smaller spheroid that is scaled by the ratio of the wavelength differences. For example, the wavelength of the fatty breast tissue for a 915 MHz signal is approximately 14 cm. The same RF signal in free space is approximately 32.8 cm. Thus, the ratio of the wavelength of the signal in the breast tissue relative to the signal in free space is approximately 0.427.

Based on this ratio, the size of such a spheroid tumor in a fatty mammary tissue region would be between 4.1 cm to 5.5 cm to enable resonance to occur for an electromagnetic signal having a frequency of 915 MHz. The resonance behavior was shown in the Air Force reports to be rather broad. An increased specific absorption rate of approximately four times can occur in a resonant body based on the increase in absorption of the electromagnetic field due to the resonant dimensions of the body relative to the wavelength of the signal in the body. The frequency bandwidth to half the peak value of the resonant phenomena was shown to be about two times the resonant frequency. Therefore, it would be expected for an RF signal at a frequency of 915 MHz that the size range of a resonant body that would at least double the SAR relative to an outer body could range from a size of 2.7 to 11 cm. This would cover the range of most primary advanced breast cancerous tumors.

Further scaling of the curve disclosed on page 101 of the SAM report shows that when an object is much smaller than the resonant size the SAR in the smaller body drops off very rapidly with frequency. For example, a spheroid diameter that is 1/5.5 in size relative to the optimum resonant diameter has a SAR that is approximately one fifth the absorption value of the body and only 5% of the SAR at resonance. So a tumor at 5.5 cm in size on resonance at 915 MHz that had a 4 to 5 times increase in SAR due to resonance would have a SAR 20 times greater than that of a 1 cm diameter tumor. Therefore, this unique resonant condition would not favor small tumor heating in the breast at 915 MHz under these modeled conditions.

Although the breast is internally dominated by mammary fatty tissues, there are glandular, ductal and lobular networks that may provide very small but higher conductivity and dielectric pathways for these microwave currents to flow and concentrate. However, these networks do not dominate the tissue construction in the breast and therefore do not significantly alter the resonant behavior and conditions. Tissue structures such as ductal and lobular networks however may themselves have selective increased SAR due to their higher conductivity, thereby causing selective pathways for the microwave currents within the breast. Also, since the breast mammary tissues themselves are more conductive that free space, it should be expected that the resonant enhancement of the specific absorption rate in a tumor relative to the absorption rate of the surrounding breast material may not be as great as it shown in the SAM report of the egg relative to air. The surrounding mammary tissue may lower the resonant behavior similar to resistive loading of a resonant electrical circuit.

The specific use of the 915 MHz frequency band that has a wavelength in mammary tissue of about 14 cm then can have the capability to excite a resonance in a higher water tissue such as a malignant tumor that has a diameter of approximately 4.5 cm. Note that even though a 3.5 cm diameter tumor does not exactly meet this criteria for the most selective tumor absorption, such a diameter at those conditions is in a state to have some resonance enhancement, but the greatest enhancement would be in a tumor with a diameter that is about ⅓$^{rd}$ of the wavelength in the mammary tissue. Fortunately, most advanced tumors of the breast that become difficult for successful surgical removal are those that exceed about 3 cm in diameter. Thus, this resonant phenomena, when properly created in these larger tumors may provide a desirable option in treating such cancerous tumors of the breast.

A linearly polarized electromagnetic signal can be used to induce a resonant behavior in a tumor. However, the use of linear polarization will tend to have a less uniform distribution of power within the tumor and even the mammary tissue and may result in undesirable hot spots in normal mammary tissue or cooler zones in the tumor. The use of elliptically or circularly polarized electromagnetic radiation to induce resonant heating in a tumor can provide more even heating.

Figure 2:
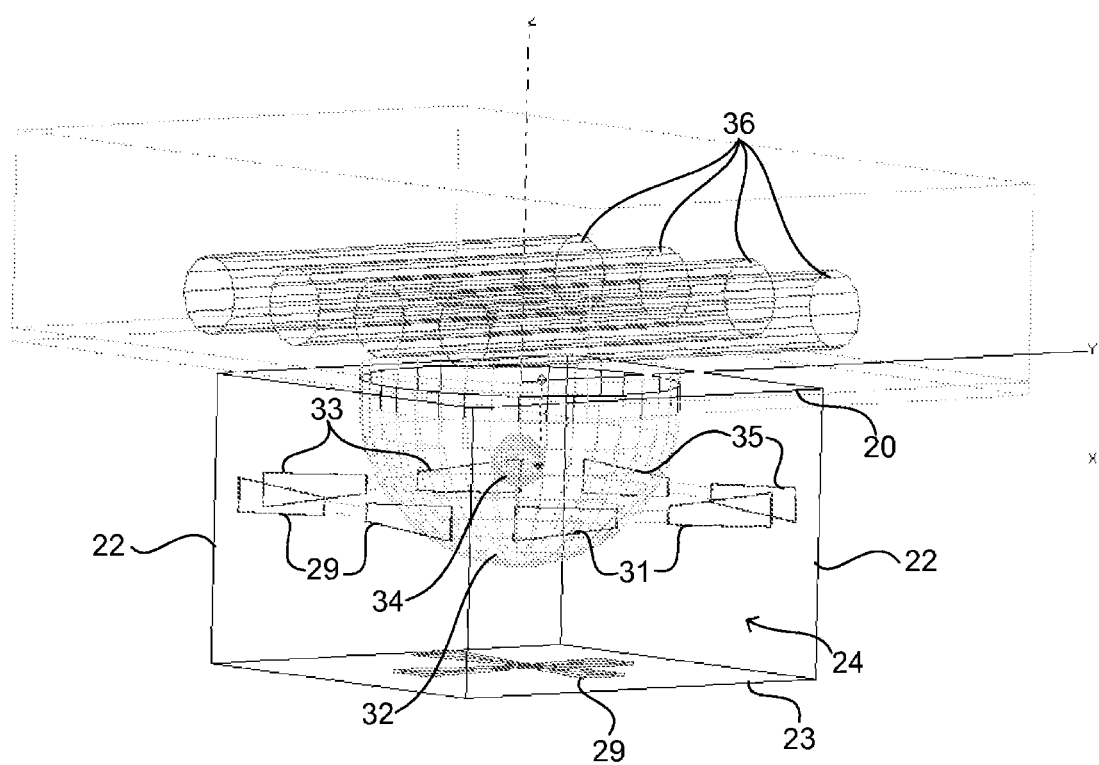
FIG. 2 is a perspective schematic illustration of an apparatus in accordance with an embodiment of the present invention.

Referring to FIGS. 1 and 2, an apparatus in one embodiment of the present invention includes an applicator body with a top peripheral surface 20, and side walls 22 with bottom wall 23 forming a cavity 24 which depends from an opening 26 in surface 20. An RF or microwave dipole antenna 28, shown as a bow tie dipole antenna, is positioned on each of the cavity walls 22 to form an antenna array surrounding the cavity 24. Additional dipole antennas 29 may be provided on bottom wall 23 as part of the antenna array. In one embodiment, the applicator can be a portable unit with the peripheral surface 20 merely forming a top surface for the applicator.

In another embodiment, the applicator can be built into a larger unit with a patient support surface 20 being a relatively comfortable supporting surface. The patient can lie on the support surface in a position so that the protruding body part of the patient can be extended into and be received in cavity 24.

In the embodiment illustrated, a female patient having breast cancer with a breast tumor is positioned with the breast 32 to be treated extending into cavity 24. The breast tumor 34 is illustrated as substantially centered in the breast 32. Patient ribs are schematically represented as 36. Cavity 24 may be filled with a dielectric fluid to improve transmission of the RF or microwave energy to the breast. While the dielectric constant of the fluid is not critical, it has been found that fluids with a dielectric constant between about two and about eighty-one may be used satisfactorily. Water, with a dielectric constant of about seventy-eight, can be used. Oils, such as mineral oil or other oils with dielectric constants of about two to about four, vegetable oils, liquid silicones, or other fluids, such as for example propylene glycol or ethylene glycol, with dielectric constants between that of oils and water can also be used. A dielectric fluid that is substantially non-ionic and has a relatively low dielectric constant can minimize heating within the fluid, thereby allowing for greater cooling at a surface of the breast tissue 34.

While the dielectric fluid(s) can be placed in the cavity 24 and come in direct contact with a breast or other body part placed in the cavity, it is usually preferred to provide a thin plastic or rubber membrane 25 in cavity 24 that separates the breast from the dielectric fluid provided in the bolus. The bolus membrane 25 can be formed by, for example, a silicone, urethane, or similar flexible membrane or film to prevent direct contact between the dielectric fluid and the body part. This protects the patient from contact with the fluid.

The dielectric fluid can also be used to control heating of the surface of the breast. The dielectric fluid may be at a lower relative temperature. Contact between the breast 32 and the bolus membrane 25 can be used to transfer excess heat from the outer breast tissue to the dielectric fluid. In one embodiment, the dielectric fluid in the cavity 24 may be circulated and cooled to provide surface cooling for the breast or other body part received in the cavity.

The size of the cavity 24 can vary. The cavity will typically be kept relatively close to the size of the body part to be received. Where a breast is to be treated, the perimeter of the cavity 24 to receive the breast works well when no more than about one and one half times the size of the base of the breast. A cavity with fifteen centimeter side walls has been found generally satisfactory for use with most breasts.

The applicator antennas 28 are connected in typical manner to a radio frequency signal source. The applicator antennas used can be of various types such as spiral antennas, waveguides, helical antennas, Tee Dipoles, and other common applicators used to radiate radio frequency radiation to heat tissue. The frequency and power output from the signal source can be controlled to provide a wavelength within the fatty mammary tissue where the diameter of the tumor is approximately $\frac{1}{3}^{rd}$ of the wavelength in the fatty tissue. For example, if the frequency of the RF signal supplied to the antennas is 915 MHz, that frequency will produce a wavelength in the normal fatty breast tissue of about 14 cm. This wavelength in the fatty mammary breast tissue will then have the capability to excite a resonance in higher water tissue, such as in malignant tumor tissue, when the diameter of the malignant tumor tissue is approximately 4.5 cm. If the tumor to be treated has a diameter of about 4.5 cm, the tumor may exhibit full resonance excitement behavior and be selectively heated by the applied electromagnetic signal relative to the fatty breast tissue.

While it has been found that full resonance behavior occurs when the tumor diameter is approximately $\frac{1}{3}^{rd}$ of the wavelength in the fatty tissue, it has also been found that significant resonant behavior is exhibited within about plus or minus twenty-five percent of the one-third dimension. Thus, although a 3.5 cm diameter tumor does not exactly meet the one-third diameter criteria for the most selective tumor absorption, such a diameter still is in a state to have some resonance enhancement, and show significant selective heating over the fatty normal breast tissue.

Since, as indicated, most advanced tumors of the breast that become difficult for successful surgical removal are those that exceed about 3 cm diameter size, a microwave frequency of 915 MHz will produce significant selective heating of such tumors in a breast. This resonant phenomena, when properly created in these relatively larger tumors, can provide a desirable option in treating such cancerous tumors of the breast. Where allowed, the frequency of the applied microwave energy can be adjusted to provide substantially an exact one-third ratio between the tumor diameter and the wavelength in the normal fatty breast tissue. The desired wavelength to be produced in the surrounding tissue to provide substantially maximum resonant phenomena in the tumor is determined by multiplying the diameter of the tumor by Π (3.14).

In one embodiment, a single antenna 28 can be used to direct radio frequency waves at a selected frequency into the breast 32 and tumor 34, as illustrated in FIG. 1. However, emitting the radio frequency waves from a single antenna will provide more heat at a side of the breast relative to the location of the antenna. To provide more even heat, a second antenna 35 located opposite the first antenna 29 can be used, as illustrated in FIG. 2. The radio frequency waves from the two antennas can be emitted in phase, thereby allowing the radio frequency waves to interfere within the cavity area 24. The two oppositely located antenna can provide heating to both a front and a back of the tumor. Additionally, an interference pattern may form, resulting in relatively hot and cold areas across the breast and tumor. Uneven absorption and reflection of the waves can also result in additional uneven heating of the tumor.

To reduce uneven heating within the cavity 24, an antenna 31 can be located with an emitting axis that is orthogonal to the emitting axis of another antenna 29. The orthogonal antennas can be tuned to be approximately 90 degrees out of phase relative to the other antenna. The resulting output from the two antennas is a substantially circularly polarized electromagnetic field within the cavity area. A total of four antennas 29, 31, 33 and 35 can be used to produce circularly polarized electromagnetic fields that substantially surround the breast. The circular polarization can effectively stir the electromagnetic fields within the chamber, thereby reducing and eliminating hot spots that can develop and occur within the heating process. If the orthogonal antennas are less than or greater than 90 degrees out of phase, the result will be elliptically polarized electromagnetic fields that can also be used to reduce and eliminate hot spots and cool spots to provide more even heat distribution within the breast 32 and tumor 34.

Figure 3A:
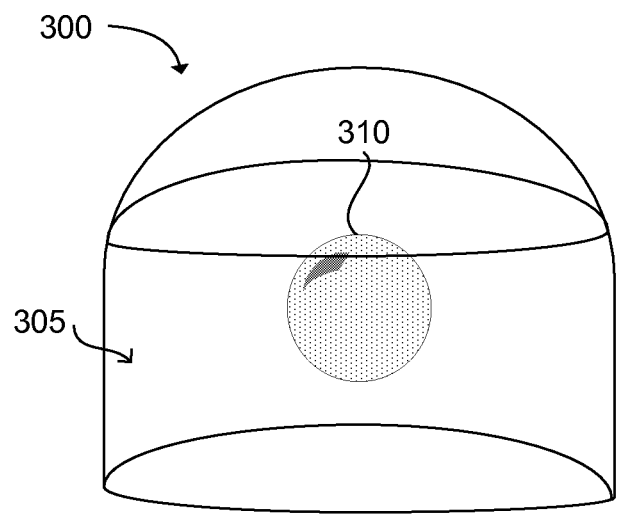
FIG. 3a is a perspective schematic illustration of a test phantom material configured to simulate a breast having a tumor in accordance with an embodiment of the present invention.

FIG. 3a shows a test phantom material 300 that was configured to simulate a breast formed substantially of fatty breast tissue 305 with a tumor 310 substantially centered therein. A phantom breast can be formed from a variety of different materials that are used to simulate the properties of the fatty breast tissue and a tumor having a higher water content. Materials are selected based on their similar properties to breast tissue in the absorption and reflection of radio frequency waves at a selected frequency, such as 915 MHz.

A plurality of different phantom breasts made of various substances were formed and tested using a test device that was configured substantially as illustrated in FIG. 2. One test phantom 300 was formed having an outer area 305 formed of paraffin wax mixed with 0.04% carbon by weight for a dielectric of 8.5 and a conductivity of 0.097 S/m. The wavelength of radio frequency waves at a frequency of 915 MHz in the outer paraffin area is about 11 cm. This wavelength divided by $\pi$ is about 3.6 cm. The inner area 310 was formed of a saline water based TX-150 gel material to simulate the makeup, electrical, and physical properties of a tumor.

Another test phantom 300 was formed using 1032 grams of wheat flour (64.5%), 464 grams of corn oil (29.9%), 4.1 grams of sodium chloride (0.256%), and 99 grams of water (6.2%) to form the outer area 305. The tumor phantom model 310 was comprised of 89.97% water, 9.8% TX-150, and 0.23% NaCl. The relative permittivity of the fat phantom is approximately 8 to 9. The Lagendijk published conductivity is 0.04 S/m.

Figure 3B:
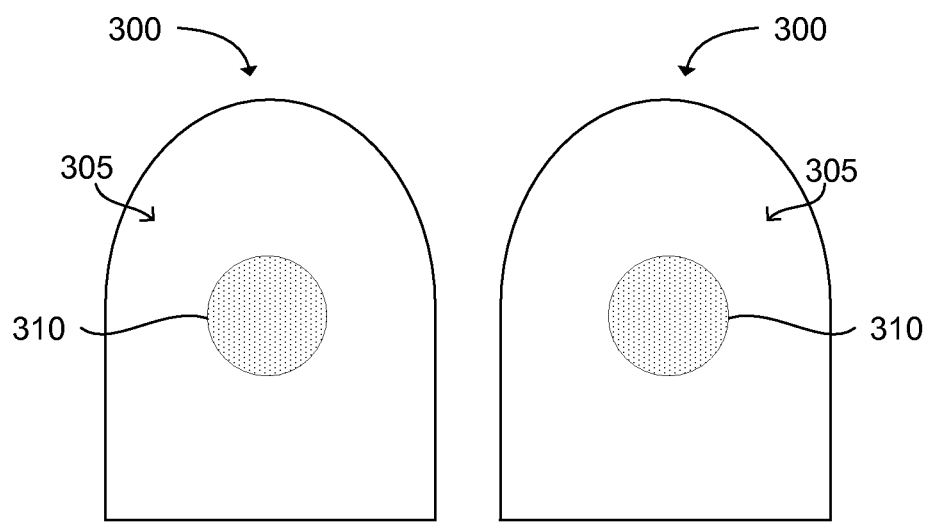
FIG. 3b is a top view of the test phantom material of FIG. 3a that is split in half to measure a temperature of the phantom material in accordance with an embodiment of the present invention.

The phantom material, as shown in FIG. 3b, can be split in two so that it can be heated and then immediately opened for test and measurement. This is done to provide an accurate measurement of an internal temperature of the simulated fatty tissue 305 and cancerous tumor 310 within the phantom breast 300.

The wax phantom and the flour phantom were both tested under a variety of conditions. In one test of the wax phantom, four power channels that were respectively coupled to the four dipole antennas 29, 31, 33 and 35, as illustrated in FIG. 2. The wax phantom was placed into the aperture 26. The four power channels were set at a relative phase of zero degrees for dipoles 29 and 35 and ninety degrees for dipoles 31 and 33, resulting in a circularly polarized field, as previously discussed. The tests were done with a bolus medium comprised of either deionized water, mineral oil, or an equivalent. The entire volume 24 of the test device can be filled with the bolus medium. Alternatively, the fluid can be confined to an area around the surface of the breast 32. In one test, the split in the phantom was oriented to be centered on dipoles 29 and 35 to allow maximum heating from the dipoles. The two halves of the phantom were separated by a thin sheet of plastic (saran wrap) to reduce evaporative cooling when the phantom was split. A similar setup was used in testing the flour phantom.

The output of the dipole antennas 29, 31, 33 and 35 can be tuned based on the type of bolus used. For example, for an oil bolus the antennas were tuned to be substantially impedance matched with the oil medium. A tuning circuit was adjusted using a Bazooka balun. A Bazooka balun is a quarter wave length of coaxial line that has the outer conductor cut away along a strip on opposite sides forming a quarter wave length of parallel line and at the tip having the center conductor short to one of the outer conductor sides to form one of the two active connection points for a balanced line. Doing this, the impedance match at 915 MHz was between 10 dB to 30 dB return loss. The tuning match was achieved by adding a capacitive shunt at a feed point of the tuning circuit.

Through testing, it was determined that use of an oil bolus with a dielectric between 2.5 and approximately 4 provided less heat absorption by the bolus compared to the use of the deionized water bolus. The lower dielectric value of the oil bolus compared with the deionized water bolus substantially reduces higher order energy modes from propagating in the bolus space. However, a water bolus may still be used if additional methods are used to prevent the higher order modes in the water. Reducing the higher order modes in the water may be accomplished using artificial dielectric modification methods such as low dielectric vanes or sheets that are cross polarized with the dipoles to present perpendicular dielectric boundaries to the electric fields in the radio frequency electromagnetic fields used to selectively heat a tumor. Higher fill factors of the breast relative to the bolus size can also reduce higher order modes. The fluid in the bolus can be circulated to provide additional cooling to the surface of the breast with which the bolus is in contact.

Figure 4:
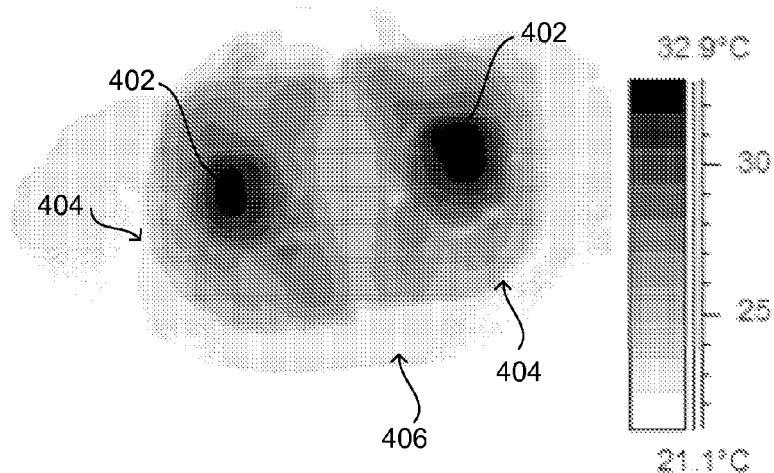
FIG. 4 is an infrared photo of a phantom breast immediately after being selectively heated, the photo showing the temperature variations for the tumor tissue and normal breast tissue representations.

An infrared camera was used to record the temperature of the split phantom after it was selectively heated as previously described. The infrared image shown in FIG. 4 shows the tumor center 402 increased in temperature from a room temperature of about 24 degrees Celsius to a temperature of 32.2 degrees Celsius for a change in temperature of 8.2 degrees Celsius. The phantom surface 404 increased from room temperature to about 27 degrees Celsius. The oil bolus fluid 406 was recorded with a maximum temperature of approximately 25.1 degrees Celsius. The image shown in FIG. 4 shows selective heating of a simulated tumor 402 in a breast equivalent phantom.

The actual amount of power that is sent to each antenna and the length of the exposure can be controlled to achieve desired results. For hyperthermia and thermal therapy systems it is common to monitor target tissue temperature during heating by invasive and at times non-invasive thermometry to provide a control parameter for power levels. In some cases, lower power can be applied for a longer period. For example, 30 watts of power may be sent to each antenna for a period of six or more minutes. Power can be reduced as needed to maintain the desired temperature for a prescribed period that may be as long as 60 minutes. In other cases, it may be desirable to apply more than 50 watts per channel for a relatively shorter period. For example, 100 watts of power may be sent to each antenna for a period of less than two minutes to reach a therapeutic temperature level which will vary with differing blood-flow. In other embodiments, different amounts of power may be sent to each antenna in the array. For example, when a tumor is not centered within the breast, it may be desirable to provide different power ratios to provide substantially even heating on each side of the tumor. The ability to monitor temperature of such a tumor and control the power to maintain a target temperature level is a common element in such applications.

Typically temperature is set to over 40 degrees Celsius and maintained for up to 60 minutes. Higher temperatures such as 60 degrees Celsius need only be maintained for less than a few minutes.

Figure 5:
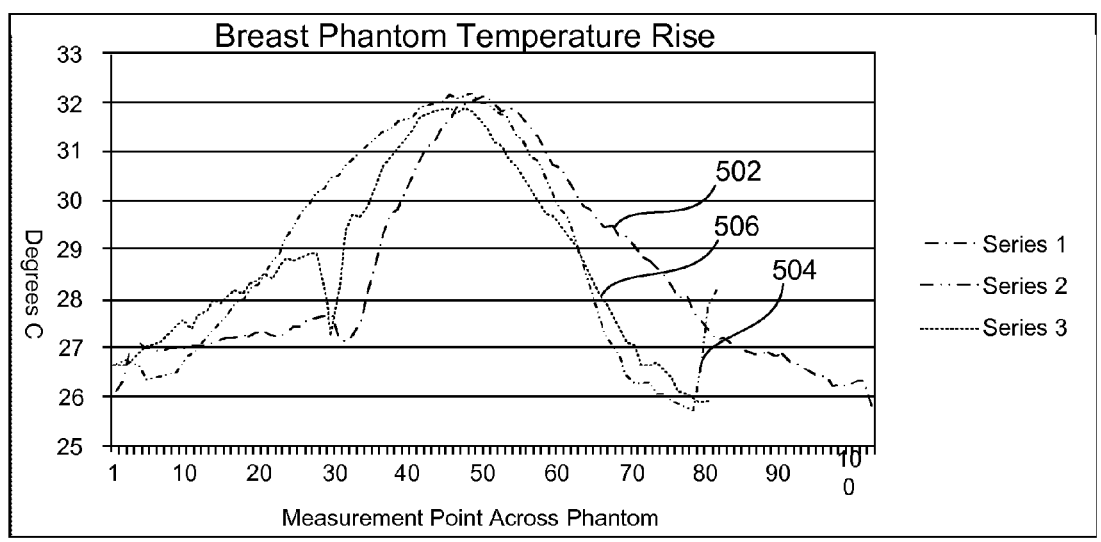
FIG. 5 is a chart showing a plurality of temperature measurements made across a phantom breast after it has been selectively heated.

FIG. 5 illustrates a diagram showing a plot of the temperature across the breast phantom. The Series 1 line 502 represents 100 temperature points taken across the wax phantom from left to right passing through the center of the tumor model. The Series 2 line 504 represents 100 temperature points taken across the phantom from back to front through the center of the tumor model. The Series 3 line 506 represents 100 temperature points taken in a diagonal from the left base of the breast phantom passing through the central tumor model and ending at the frontal side surface of the wax breast phantom. Each of the series lines show that the temperature dramatically increases at a center of the phantom, where the tumor model is located, thereby showing selective heating of a tumor in the breast equivalent phantom.

Additional testing was performed, with each test showing a significant heating of the tumor relative to the surrounding tissue. The following table summarizes the temperature change of the tumor material in the paraffin phantom and the surface temperature of the phantom as a result of short term heating experiments to measure where the power is being primarily absorbed.

| Tests | Tumor Max Temp. Change | Surface Max Temp Change |
| --- | --- | --- |
| 1 | 8.2° C. | 3.0° C. |
| 2 | 11.8° C. | 3.9° C. |
| 3 | 10.7° C. | 5.4° C. |
| 4 | 8.8° C. | 2.7° C. |

The average ratio from these tests of the tumor maximum temperature rise versus the average maximum temperature rise on the phantom surface is 9.875/3.75=2.63. Thus, a tumor located in a fatty breast tissue can be selectively heated using radio frequency waves when the tumor has a diameter that is around $1/3^{rd}$ of the wavelength of a radio frequency electromagnetic field in the fatty tissue. In other words, the wavelength of the radio frequency waves in the fatty breast tissue will be about three times a width of the tumor for optimal resonant heating. Of course, resonant heating can still be attained within a range of wavelengths. The wavelength of the radio frequency waves in the fatty tissue may be +/- about 25% of the optimal length, or in other words about 3.75 times a diameter of the tumor to about 2.25 times a diameter of the tumor. Alternatively, a single frequency such as 915 MHz can be used to provide resonant heating of tumors. The tumor can optimally be about 1/3 of the wavelength of the radio frequency waves in the fatty tissue. At 915 MHz, the wavelength in the fatty tissue is approximately 14 cm. Thus, a tumor within a range of 25% from the optimal size will have a diameter of about 3.5 cm to 5.25 cm. Some resonant heating may be attained for tumors within a 50% range from the optimal size of 4.6 cm. Thus, selective heating can be accomplished for a tumor or another deposit such as a cyst, or high conductivity implant having a diameter of about 2.3 cm to over 7 cm, with an increased amount of selective heating when the tumor has a size of about 4.5 cm. Additional preparation of a deposit can increase selective heating, as further discussed below.

Figure 6:
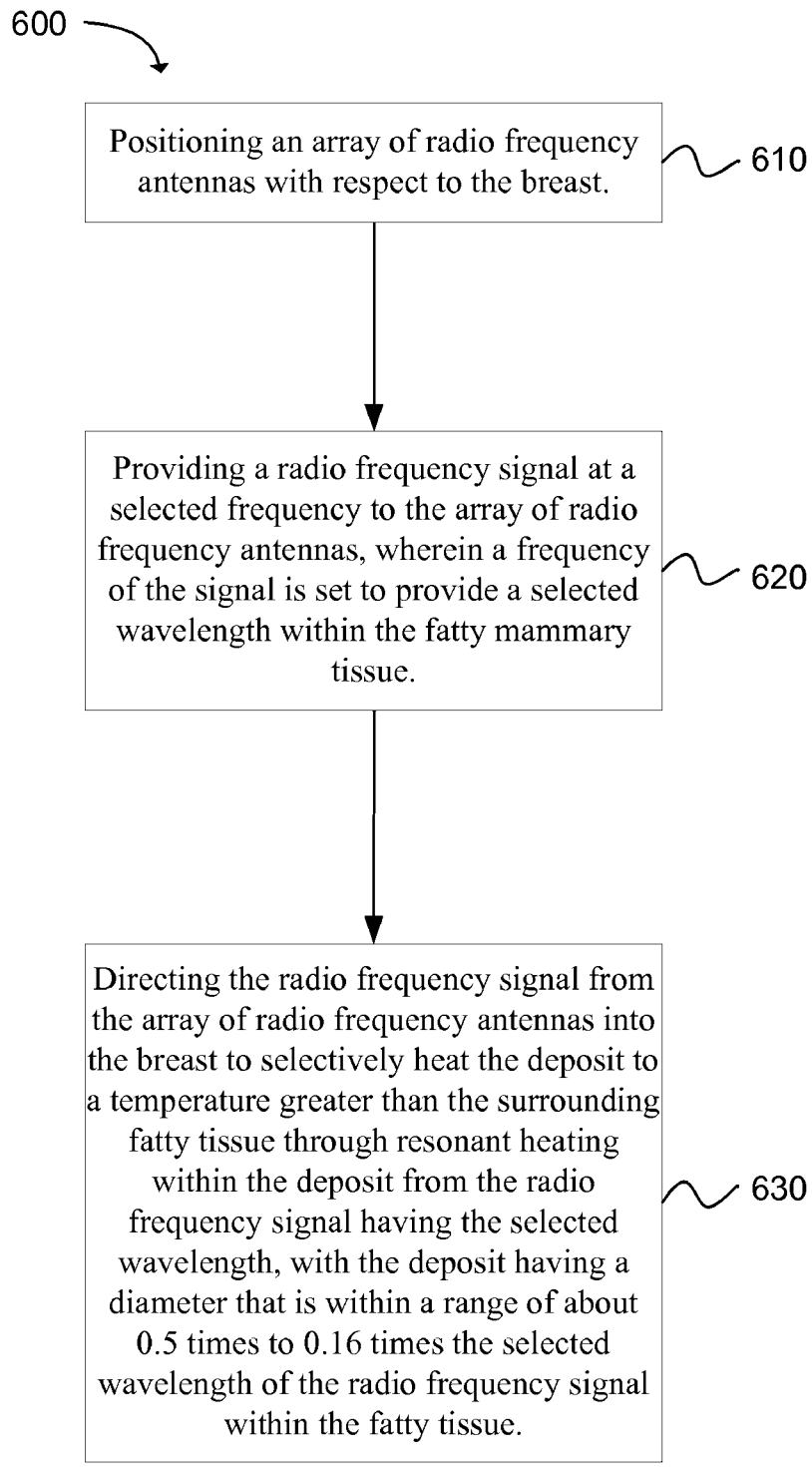
FIG. 6 is a flow chart depicting a method of selectively heating a deposit in a breast in accordance with an embodiment of the present invention.

In another embodiment, a method 600 of selectively heating a deposit in a breast having fatty mammary tissue surrounding the deposit is disclosed, as depicted in the flow chart in FIG. 6. The deposit can be any non-native body within the breast, such as a cancerous tumor, cyst, or high conductivity implant. The method includes the operation of positioning 610 an array of radio frequency antennas with respect to the breast. The antennas in the array can be positioned around the breast to provide substantially even heating of the deposit within the breast. In one embodiment, at least one antenna in the array can be positioned to emit waves perpendicular to another antenna in the array and 90 degrees out of phase to provide substantially circular polarization of the electromagnetic field in the breast and deposit. In one embodiment, the array can be comprised of two antennas that are substantially in phase and two antennas that are positioned to direct orthogonal waves that are about 90 degrees out of phase with the first two antennas to provide the circularly polarized electromagnetic field. Additional antennas may also be used, such as antennas located below the breast and tumor.

The method 600 further includes the operation of directing 620 the radio frequency signal from the array of radio frequency antennas into the breast to selectively heat the deposit to a temperature greater than the surrounding fatty tissue through resonant heating within the deposit from the radio frequency signal having the selected wavelength. The deposit can have a diameter that is within a range of about 0.5 times to 0.16 times the selected wavelength of the radio frequency signal within the fatty tissue. A radio frequency signal generator can be used to provide the radio frequency signal at the selected frequency.

In one embodiment, a radio frequency signal having a frequency of 915 MHz may be used. Substantially optimal resonant heating can be obtained when a deposit such as a cancerous tumor, cyst, or high conductivity implant has a diameter that is approximately 1/3 of the wavelength of the signal in the fatty breast tissue.

To increase the resonant heating effect to the tumor, the conductivity or dielectric constant of the tumor may be changed by injecting material into the tumor. For example, material such as a saline solution may be injected to increase the conductivity or dielectric constant of the tumor relative to the fatty breast tissue. The saline solution may also act as a carrier for additional material, such as carbon nanotubes or other types of material that can increase the conductivity or dielectric constant of the tumor. The carbon nanotubes or other material can be injected into the tumor to substantially increase its conductivity, thereby increasing the selective heating of the tumor relative to the surrounding tissue to a level greater than the average 2.63 times increase shown in the test data above.

The present invention is not limited to selectively heating tumors. Other types of deposits within a protruding body portion can also be selectively heated using a proper wavelength of radio frequency waves to provide resonant heating of the deposit within the body portion. For example, after a lumpectomy is performed to remove a tumor, a balloon like device can be implanted into the area where the tumor was located. The balloon like device may be inflated and used in additional radiation or heat treatments. In one embodiment, the balloon can be inflated with a selected material having a desired conductivity and dielectric constant relative to the surrounding fatty breast tissue to enable the material in the balloon to be optimally selectively heated using radio frequency waves, as previously discussed. In one embodiment, an implantable device such as a Mammosite® can be used to selectively heat an area within the breast where a tumor was previously removed. Alternatively, the balloon and material may be inserted prior to the tumor's removal and used to apply heat to the tumor.

The heating described can be used to selectively heat a breast tumor to enhance tumor therapeutic affects by other cancer treatments such as radiation or chemotherapy (such as selective heat release of liposome encapsulated chemotherapy), or both. As one non-limiting example of a combined therapy/hyperthermia treatment, a traditional cancer therapy (e.g., chemotherapy and/or radiation) is given to a patient and followed by a computed tomography (CT) scan or other appropriate scanning technique to locate the precise location of the tumor within the tissue. The hyperthermia treatment is then given as described hereinabove. After the final hyperthermia treatment is given, a radiation oncologist measures the tumor shrinkage by any suitable means, and recommends the least invasive type of surgery to remove the tumor. Surgery is followed by additional therapy and hyperthermia treatment, if one or both procedures are indicated at this stage, to kill any undetected cancer cells in the tissue.

It can be appreciated that the embodiments disclosed hereinabove have potential applications outside the immediate scope of cancer therapy, such as cellular necrosis, chemical reaction kinetics, and catalysis. It will also be understood only examples of the invention have been shown and described and that various details of the invention may be changed without departing from the scope of the invention. Furthermore, the foregoing description is for the purpose of illustration only, and not for the purpose of limitation.

What is claimed is:

1. An apparatus for providing hyperthermia treatments to a breast having fatty mammary tissue surrounding a deposit in the breast, comprising:
   a cavity for receiving the breast therein substantially without distortion of the breast; and
   a first radio frequency antenna operable to direct a radio frequency signal at a selected frequency into the breast such that the radio frequency signal will have a selected wavelength to selectively heat the deposit to a temperature greater than the surrounding fatty mammary tissue through resonant heating within the deposit from the radio frequency signal when a diameter of the deposit is within a range of about 0.5 times to 0.16 times the wavelength of the radio frequency signal within the fatty mammary tissue.

2. The apparatus of claim 1, further comprising a radio frequency signal generator operable to generate the radio frequency signal at the selected frequency.

3. The apparatus of claim 1, wherein the deposit is a cancerous tumor.

4. The apparatus of claim 1, wherein the deposit is an insertable device.

5. The apparatus of claim 1, wherein the selected frequency of the radio frequency signal is about 915 MHz.

6. The apparatus of claim 1, wherein the deposit has a diameter of in a range of about 2.3 to 7 centimeters.

7. The apparatus of claim 1, wherein the deposit has a diameter in a range of about 3.5 to 5.75 centimeters.

8. The apparatus of claim 1, wherein the deposit is injected with material to increase at least one of a dielectric constant and a conductivity of the deposit to increase the resonant heating from the radio frequency signal.

9. The apparatus of claim 1, further comprising a second antenna located on an opposite side of the cavity from the first antenna, with both first and second antennas directed at the breast to provide constructive interference waves within the breast and more evenly heat opposite sides of the deposit.

10. The apparatus of claim 9, further comprising a third antenna, wherein the third antenna is positioned to emit a radio frequency signal into the breast that is directed perpendicular to the radio frequency signal of the first antenna and is approximately 90 degrees out of phase with the radio frequency signal from the first antenna to cause the radio frequency signals from the first and third antennas to be substantially circularly polarized to provide more even distribution of radio frequency electromagnetic radiation within the container and more even heating of the deposit.

11. The apparatus of claim 10, further comprising a fourth antenna, wherein the fourth antenna is positioned to emit a radio frequency signal into the breast that is directed perpendicular to the radio frequency signal of the second antenna and is approximately 90 degrees out of phase with the radio frequency signal from the second antenna to cause the radio frequency signals from the second and fourth antennas to be substantially circularly polarized to provide more even distribution of radio frequency electromagnetic radiation within the breast and more even heating of the deposit.

12. The apparatus of claim 11, wherein the first, second, third and fourth antennas are selected from the group consisting of a dipole antenna, a bow tie dipole antenna, a spiral antenna, a waveguide, a helical antenna, and a tee dipole.

13. The apparatus of claim 11, further comprising a fifth antenna positioned at a bottom of the cavity and operable to emit a substantially circularly polarized radio frequency signal toward the breast.

14. The apparatus of claim 11, wherein the phase difference between the first and third antennas and the second and fourth antennas is less than or greater than 90 degrees to provide elliptical polarization of radio frequency electromagnetic radiation within the breast.

15. The apparatus of claim 1, further comprising a fluid filled bolus positioned in the cavity between the breast and the first radio frequency antenna.

16. The apparatus of claim 15, wherein the fluid in the fluid filled bolus is a substantially non-ionic fluid having a dielectric constant less than ten.

17. The apparatus of claim 15, wherein the fluid in the fluid filled bolus is selected from the group consisting of mineral oil, vegetable oil, propylene glycol, ethylene glycol, deionized water, liquid silicon.

18. An apparatus for providing hyperthermia treatments to a protruding body portion having fatty tissue surrounding a deposit in the protruding body portion, comprising:
   a cavity for receiving the protruding body portion therein;
   a radio frequency signal generator operable to generate a radio frequency signal at a selected frequency such that the radio frequency signal will have a selected wavelength within the fatty tissue; and
   a radio frequency antenna array operable to direct a circularly polarized radio frequency electromagnetic field into the breast to selectively heat the deposit to a temperature greater than the surrounding fatty tissue through resonant heating within the deposit from the radio frequency signal having the selected wavelength, with the deposit having a diameter that is within a range of about 0.41 to 0.25 times the selected wavelength of the radio frequency signal within the fatty tissue.

19. A method of selectively heating a deposit in a breast having fatty mammary tissue surrounding the deposit in the breast, comprising:
   positioning an array of radio frequency antennas with respect to the breast substantially without distorting the breast;
   providing a radio frequency signal at a selected frequency to the array of radio frequency antennas, wherein a frequency of the signal is set to provide a selected wavelength within the fatty mammary tissue; and directing the radio frequency signal from the array of radio frequency antennas into the breast to selectively heat the deposit to a temperature greater than the surrounding fatty tissue through resonant heating within the deposit from the radio frequency signal having the selected wavelength, with the deposit having a diameter that is within a range of about 0.5 times to 0.16 times the selected wavelength of the radio frequency signal within the fatty tissue.

20. A method as in claim 19, wherein directing the radio frequency signal further comprises directing the radio frequency signal from the array of radio frequency antennas to provide a circularly polarized electromagnetic field at the selected wavelength within the deposit to provide substantially even resonant heating of the deposit to enable the deposit to be heated to a substantially higher temperature than the surrounding fatty mammary tissue.

21. A method as in claim 19, further comprising directing the radio frequency signal from the array of radio frequency antennas into the breast to selectively heat the deposit, wherein the deposit is selected from the group consisting of a cancerous tumor, a cancerous tumor injected with material to increase at least one of a dielectric constant and a conductivity of the deposit, and an insertable device.

\* \* \* \* \*